United States Patent [19]

Warriner

[11] Patent Number: Plant 7,650

[45] Date of Patent: Sep. 17, 1991

[54] ROSE PLANT JACMISS

[75] Inventor: William A. Warriner, Tustin, Calif.

[73] Assignee: Bear Creek Gardens, Inc., Medford, Oreg.

[21] Appl. No.: 513,492

[22] Filed: Apr. 23, 1990

[51] Int. Cl.[5] ..... A01H 5/00

[52] U.S. Cl. ..... Plt./9

[58] Field of Search ..... Plt. 9, 1, 2, 3, 5, Plt./7, 8

*Primary Examiner*—Howard J. Locker

*Attorney, Agent, or Firm*—Klarquist, Sparkman, Campbell, Leigh & Whinston

[57] ABSTRACT

A miniature class rose plant having compact spreading growth habit, high, nearly constant production of flowers, attractive light pink flower color, and disease resistant glossy foliage.

1 Drawing Sheet

The present invention relates to a new and distinct variety of rose plant of the miniature class which was originated by me by crossing the variety Over the Rainbow, with the variety Lavender Lace.

The primary objective of this breeding was to produce a new rose variety having the vigor and flower production of the female parent, Over the Rainbow, coupled with the dwarf habit and glossy small foliage of the male parent, Lavender Lace. The objective was substantially achieved along with other desirable improvements as evidenced by the following unique combination of characteristics which are outstanding in the new variety and which distinguish it from its parents as well as from all other varieties of which I am aware:

1. Compact spreading habit.
2. High, nearly constant production of flowers.
3. Attractive light pink flower color.
4. Disease resistant glossy foliage.

Asexual reproduction of this new variety by budding, as performed at Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color terminology in accordance with the Royal Horticultural Society (London) Colour Chart, except where ordinary dictionary significance of color is indicated.

Parentage:

*Seed parent.*—Over the Rainbow.

*Pollen parent.*—Lavender Lace.

Classification:

*Botanical.*—*Rosa hybrida.*

*Commercial.*—Miniature.

FLOWER

Observations made from specimens grown in a garden in Somis, Calif., from June to October, 1989.

Blooming habit: Continuous.

Bud:

*Size.*—About ½ inch long when the petals start to unfurl.

*Form.*—The bud form is long, pointed ovoid.

*Color.*—When sepals first divide, the bud color is White Group 155D with Red Group 49C to D at the tip of the flower. When half blown, the upper sides of the petals are Red Group 49C to D fading to White Group 155D at the petal edges and the lower sides of the petals are White Group 155D.

*Sepals.*—Color: Green Group 138B. Surface texture: Covered with fine hairs. There are three normally appendaged sepals. There are two unappendaged sepals with hairy edges.

*Receptacle.*—Color: Medium green. Shape: Funnel. Size: Medium. Surface: Smooth.

*Peduncle.*—Length: Short, averaging less than about ½ inch. Surface: Smooth. Color: Medium green with some bronze coloration. Strength: Stiff, erect.

Bloom:

*Size.*—Small. Average open diameter is 1¼ inches.

*Borne.*—Singly and several together, in pyramidal clusters.

*Stems.*—Short, strong.

*Form.*—When first open, bloom has high center. Bloom flattens as it opens, with outer petals curling back in a quill fashion.

*Petalage.*—Number of petals under normal conditions: 50 to 60.

*Color.*—The upper side of the petals is Red Group 49C to D fading to White Group 155D at flower edges. The reverse side of the petals is White Group 155D. The base of petals has a small greenish white half moon at the point of attachment. The major color on the upper side is Red Group 49D.

*Variegations.*—None.

*Discoloration.*—No general tonality change at the end of the first day. At the end of the third day, gradual fading to White Group 155D.

*Fragrance.*—Slight.

Petals:

*Texture.*—Thin.

*Shape.*—Deltoid.

*Form.*—Tips slightly recurved, edges slightly quilled.

*Arrangement.*—Imbricated, with many petaloids in the center.

*Persistence.*—Petals drop off clearly before drying.

*Lastingness.*—On the plant: Fair, about 3 to 5 days. As a cut flower: Fair, about 3 to 5 days.

Reproductive parts:

*Anthers.*—Size: Medium. Quantity: Many. Color: Reddish brown. Arrangement: Regular around styles, mixed with petaloids.

*Filaments.*—Color: White.

*Pollen.*—Color: Gold yellow.

*Styles.*—Color: Red.

*Stigmas.*—Color: Red.

Plant form: Bush.

Plant growth: Vigorous, dwarf, compact, spreading. The plant grows as wide as it does tall (about 18 inches × 18 inches).

Foliage: Number of leaflets on normal mid-stem leaves: 5.

*Size.*—Small, about 2 to 2½ inches in length.

*Quantity.*—Normal.

*Color.*—New foliage: Reddish. Old foliage: Medium green.

Leaflets:

*Shape.*—Pointed oval.

*Texture.*—Upper side: Glossy, smooth.

*Edge.*—Serrated.

*Serration.*—Single, small.

*Petiole rachis.*—Color: Reddish.

*Petiole underside.*—Smooth.

*Stipules.*—Long, bearded.

*Disease resistance.*—Resistant to powdery mildew under normal growing conditions at Somis, Calif. The variety is also resistant to rust in Somis, but susceptible to blackspot.

Wood:

*New wood.*—Color: Reddish. Bark: Smooth.

*Old wood.*—Color: Green.

Prickles:

*Quantity.*—Ordinary quantity on main canes from base and on laterals from main canes.

*Form.*—Straight to slightly hooked downward.

*Color when young.*—Red.

Small prickles:

*Quantity.*—None on main stalks and laterals.

I claim:

1. A new and distinct variety of rose plant of the miniature class, substantially as herein shown and described, characterized particularly as to novelty by the unique combination of its distinctive compact spreading habit of growth, disease resistant glossy foliage, attractive flower form and light pink color, and its high, nearly constant production of flowers.

* * * * *

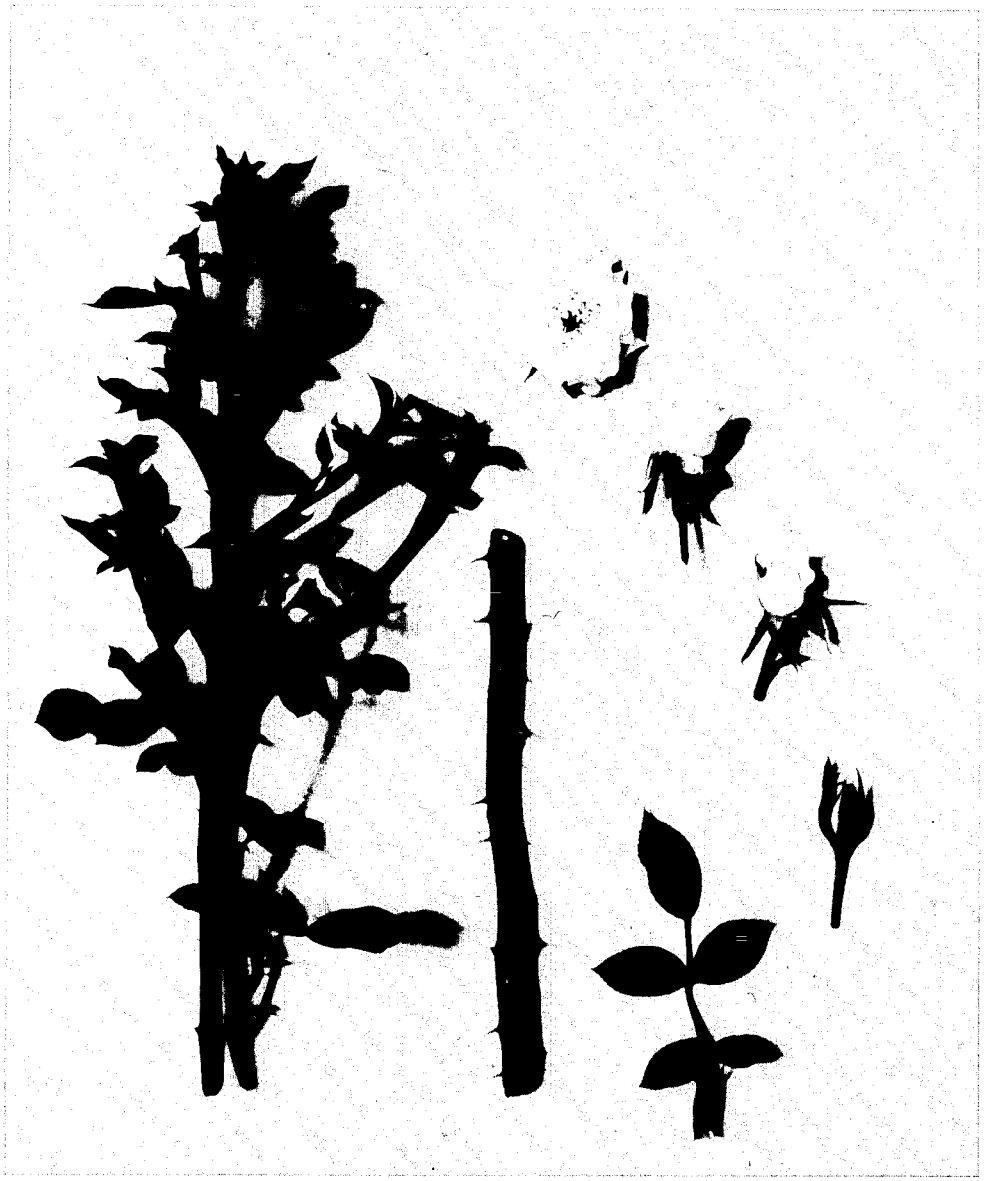

UNITED STATES PATENT AND TRADEMARK OFFICE

CERTIFICATE OF CORRECTION

PATENT NO. : PP 7,650

DATED : September 17, 1991

INVENTOR(S) : WILLIAM A. Warriner

It is certified that error appears in the above-identified patent and that said Letters Patent is hereby corrected as shown below:

Column 3, line 3, "clearly" should be --cleanly --.

Column 4, line 11, (missing) should be --Bark: smooth.--.

Signed and Sealed this

Twenty-second Day of June, 1993

*Attest:*

Michael K. Kirk

MICHAEL K. KIRK

*Attesting Officer*

*Acting Commissioner of Patents and Trademarks*